(12) United States Patent
Johnston et al.

(10) Patent No.: US 10,895,549 B2
(45) Date of Patent: Jan. 19, 2021

(54) ELECTROCHEMICAL SENSOR

(71) Applicant: PALINTEST LIMITED, Gateshead (GB)

(72) Inventors: Simon Johnston, Chollerton (GB); Stephen William Birch, Tyne & Wear (GB)

(73) Assignee: Palintest Limited, Gateshead (GB)

( * ) Notice: Subject to any disclaimer, the term of this patent is extended or adjusted under 35 U.S.C. 154(b) by 190 days.

(21) Appl. No.: 16/082,569

(22) PCT Filed: Mar. 27, 2017

(86) PCT No.: PCT/GB2017/050818
§ 371 (c)(1),
(2) Date: Sep. 6, 2018

(87) PCT Pub. No.: WO2017/178784
PCT Pub. Date: Oct. 19, 2017

(65) Prior Publication Data
US 2019/0033246 A1    Jan. 31, 2019

(30) Foreign Application Priority Data
Apr. 11, 2016 (GB) .................................. 1606111.1

(51) Int. Cl.
*G01N 27/30* (2006.01)
*G01N 33/18* (2006.01)
*G01N 27/406* (2006.01)

(52) U.S. Cl.
CPC ......... *G01N 27/307* (2013.01); *G01N 27/308* (2013.01); *G01N 27/406* (2013.01); *G01N 33/182* (2013.01)

(58) Field of Classification Search
None
See application file for complete search history.

(56) References Cited

U.S. PATENT DOCUMENTS 6,419,809 B1    7/2002   Suzuki et al.
2009/0321278 A1   12/2009   Birch et al.

FOREIGN PATENT DOCUMENTS

WO   WO-2007/026152 A1   3/2007
WO   WO-2012/010864 A1   1/2012

OTHER PUBLICATIONS

International Preliminary Report on Patentability for PCT/GB2017/050818 dated Oct. 25, 2018.
International Search Report for PCT/GB2017/050818, ISA/EP, Rijswijk, NL, dated Jun. 20, 2017.
Written Opinion of the ISA for PCT/GB2017/050818, ISA/EP, Rijswijk, NL, dated Jun. 20, 2017.
Search Report under Section 17(5) for priority application GB1606111.1, UKIPO, Newport, South Wales, dated Sep. 23, 2016.
John N. Myers et al: "Development of an Automated On-line Electrochemical Chlorite Ion Sensor", Talanta, Elsevier, Amsterdam, NL, vol. 94, Mar. 15, 2012 (Mar. 15, 2012), pp. 227-231, XP028489284, ISSN: 0039-9140, DOI: 10.1016/J.TALANTA.2012.03.026 [retrieved on Mar. 21, 2012].

(Continued)

*Primary Examiner* — J. Christopher Ball
(74) *Attorney, Agent, or Firm* — Harness, Dickey & Pierce, P.L.C.

(57) ABSTRACT

The present invention relates to an electrochemical sensor for determining the presence or quantity (eg concentration) of an oxidant of interest in an aqueous solution.

26 Claims, 9 Drawing Sheets

(56) References Cited

OTHER PUBLICATIONS

Libuse Trnkova et al: "Amperometric Sensor for Detection of Chloride Ions", Sensors, vol. 8, No. 9, Sep. 15, 2008 (Sep. 15, 2008), pp. 5619-5636, XP055378833, DOI: 10.3390/s8095619.
Jonathan P. Metters et al., "Fabrication of co-planar screen printed microband electrodes", Analyst 2013, 138, pp. 2516-2521, DOI:10.1039/c3an00268c, The Royal Society of Chemistry 2013.

(A)

(B)

ELECTROCHEMICAL SENSOR

CROSS-REFERENCE TO RELATED APPLICATIONS

This application is a 371 U.S. National Stage of International Application No. PCT/GB2017/050818, filed Mar. 27, 2017, which claims priority to British Patent Application No. GB 1606111.1, filed Apr. 11, 2016. The entire disclosures of the above applications are incorporated herein by reference.

The present invention relates to an electrochemical sensor for determining the presence or quantity (eg concentration) of an oxidant of interest in an aqueous solution.

Electrochemical sensors of the type disclosed in WO-A-2007/026152 have been developed with an overall area of working electrode which is small. These sensors are manufactured with working electrodes within the dimensional range (50-400 micron) for them to be considered to be microelectrodes. Microelectrodes have a number of advantages over macroelectrodes including faster mass transport rates, lower ohmic drop and improved diffusion provided that the gap between adjacent electrodes is sufficient to ensure diffusional independence (ie the proximity of the adjacent electrode does not limit the current at its nearest neighbours).

In these electrochemical sensors, a reagent formulation is dried on the electrode surface to provide the chemical components essential for specific ion electroanalysis. Once the electrochemical sensor is immersed in a test solution, dissolution takes place to give rise to natural convection of the reagent formulation from the surface into the bulk solution. The large difference in localised ionic strength between the boundary layer adjacent to the surface and the bulk solution gives rise to a convective plume emanating away from the surface. This introduces variability in the current measured over time and has a disruptive effect on chronoamperometric techniques.

WO-A-2007/026152 discloses that the small total current passed by a microelectrode makes it possible to operate in a solution without the addition of supporting electrolyte. This limits the number of operational steps required and is convenient for the user. It also prevents measurement errors which might otherwise be caused by the incorrect addition of a supporting electrolyte.

The present invention is based on the recognition that depositing a supporting electrolyte onto the surface of an electrochemical sensor away from the working electrode limits the formation of convective plumes of reagent and improves measurement capability.

Thus viewed from a first aspect the present invention provides an electrochemical sensor for determining the presence or quantity of an oxidant of interest in an aqueous solution comprising:
  an elongate substrate layer having a first end opposite to a second end;
  first, second and third conductive tracks deposited axially onto the substrate layer in a parallel mutually spaced apart relationship, wherein the first conductive track constitutes a reference electrode, wherein on the second conductive track near to the second end of the substrate layer is a carbon deposit whereby to constitute a counter electrode and on the third conductive track near to the second end of the substrate layer is a carbon deposit whereby to constitute a working electrode, wherein each of the first, second and third conductive tracks terminates near to the first end of the substrate layer in an electrical contact;
  a non-conductive layer deposited on the first, second and third conductive tracks, wherein the non-conductive layer is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposit of the third conductive track through an array of apertures;
  a reagent formulation deposited on or near to the surface of the working electrode, wherein the reagent formulation includes a reductant; and
  a deposit of a supporting electrolyte deposited on the non-conductive layer.

The reagent formulation provides the chemical components including the reductant essential for electroanalysis of a specific oxidant of interest.

The first conductive track may be between the second conductive track and the third conductive track.

Preferably the amount of the deposit of supporting electrolyte deposited on the non-conductive layer is sufficient in use to substantially remain within a boundary layer region at the surface of the non-conducting layer (eg over a measurement period such as a measurement period of about two minutes).

Preferably the amount of the deposit of supporting electrolyte deposited on the non-conductive layer is in excess of $2.0 \times 10^{-6}$ moles, particularly preferably in excess of $2.4 \times 10^{-6}$ moles, more preferably in excess of $3.2 \times 10^{-6}$ moles (eg about $4.0 \times 10^{-6}$ moles).

Preferably the amount of the deposit of supporting electrolyte deposited on the non-conductive layer is in the range $2.1 \times 10^{-6}$ to $6.0 \times 10^{-6}$ moles, particularly preferably in the range $2.4 \times 10^{-6}$ to $5.6 \times 10^{-6}$ moles, more preferably in the range $3.2 \times 10^{-6}$ to $4.8 \times 10^{-6}$ moles.

Preferably the deposit of supporting electrolyte deposited on the non-conductive layer is depositable from an aqueous solution of the supporting electrolyte with a molarity in excess of 0.626 mol/l, particularly preferably in excess of 0.800 mol/l, more preferably in excess of 1.07 mol/l (eg about 1.25 mol/l).

Preferably the deposit of supporting electrolyte deposited on the non-conductive layer is depositable from an aqueous solution of the supporting electrolyte with a molarity in the range 0.63 to 1.90 mol/l, particularly preferably 0.73 to 1.75 mol/l, more preferably in the range 1.00 to 1.50 mol/l.

Typically the supporting electrolyte is inert (eg does not participate in the redox reaction).

Preferably the supporting electrolyte is potassium chloride.

The deposit of a supporting electrolyte may be deposited on a region of the non-conductive layer between (eg exclusively between) the fully exposed carbon deposit on the second conductive track and the partially exposed third conductive track.

In a preferred embodiment, the deposit of a supporting electrolyte is deposited on a region of the non-conductive layer between (eg exclusively between) the fully exposed carbon deposit on the second conductive track and the fully exposed first conductive track.

The deposit of a supporting electrolyte may be one or more doses of the supporting electrolyte deposited discretely on the non-conductive layer.

Preferably the deposit of a supporting electrolyte is a plurality of doses of the supporting electrolyte deposited discretely on the non-conductive layer.

The plurality of doses may be 10 to 20 doses (eg 16 doses). Typically the amount of the plurality of doses is 3 to 4 µl (eg about 3.2 µl).

Preferably the plurality of doses is deposited in a parallel mutually spaced apart relationship to the first, second and third conductive track.

The array of apertures may be fabricated in the non-conductive layer by a mechanical, chemical or physical removal technique such as ablation (eg photoablation) or etching. The array of apertures may be fabricated in the non-conductive layer by screen printing.

Each aperture may have a substantially regular shape. Typically the apertures are uniformly shaped. Each aperture may be substantially circular or non-circular (eg rectangular or square).

Preferably each aperture is substantially circular.

The array may adopt any suitable pattern (eg cubic or rectangular). The array may comprise 10 to 500 apertures, preferably 50 to 200 apertures, more preferably 80 to 120, most preferably about 95 apertures.

Preferably each aperture has a dimension (eg diameter) in the range 50 to 400 µm (eg about 350 µm).

Each aperture may be elongate (eg linear). Each elongate aperture may be substantially parallel to the first, second and third conductive track (eg vertical).

Preferably each elongate aperture is substantially perpendicular to the first, second and third conductive track (eg horizontal).

In a preferred embodiment, each aperture of the array of apertures is substantially rectangular (eg a microband). For example, each aperture may be microscopic in width (eg about 50 microns) and macroscopic in length.

In a preferred embodiment, the array of apertures is a substantially rectangular array.

In a preferred embodiment, the electrochemical sensor further comprises:

a fourth conductive track deposited axially onto the substrate layer, wherein the first, second, third and fourth conductive track are in a parallel mutually spaced apart relationship, wherein on the fourth conductive track near to the second end of the substrate layer is a carbon deposit whereby the third and fourth conductive tracks constitute a pair of working electrodes, wherein the first and second conductive tracks are flanked by the third and fourth conductive tracks, wherein each of the first, second, third and fourth conductive tracks terminates near to the first end of the substrate layer in an electrical contact, wherein the non-conductive layer is deposited on the first, second, third and fourth conductive tracks and is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposits of the third and fourth conductive tracks through an array of apertures, wherein the reagent formulation is deposited on or near to the surface of either or both of the pair of working electrodes.

Preferably the plurality of doses is deposited in a parallel mutually spaced apart relationship to the first, second, third and fourth conductive track.

The deposit of a supporting electrolyte may be deposited on a region of the non-conductive layer between (eg exclusively between) the fully exposed first conductive track and the partially exposed fourth conductive track.

The deposit of a supporting electrolyte may be deposited on a region of the non-conductive layer which is not between any of the fully exposed carbon deposit on the second conductive track, the partially exposed third conductive track, the fully exposed first conductive track and the partially exposed fourth conductive track.

Each aperture may be elongate (eg linear). Each elongate aperture may be substantially parallel to the first, second, third and fourth conductive track (eg vertical).

Preferably each elongate aperture is substantially perpendicular to the first, second, third and fourth conductive track (eg horizontal).

The pair of working electrodes may be a first working electrode connected to a first current amplifier and a second working electrode connected to a second current amplifier.

The non-conductive layer may be fabricated by a known deposition or growth technique such as printing (eg screen printing, silk screen printing, ink-jet printing or thick film printing), casting, spinning, sputtering, lithography, vapour deposition, spray coating or vacuum deposition. Preferably the non-conductive layer is fabricated by screen printing. The non-conductive layer may be composed of a non-conductive ink.

Each conductive track may be fabricated by a known deposition or growth technique such as printing (eg screen printing, silk screen printing or thick film printing), casting, spinning, sputtering, lithography, vapour deposition, spray coating or vacuum deposition. Each conductive track may be composed of an inert metal such as gold, silver or platinum. Each conductive track may be composed of a conductive ink such as silver or silver/silver chloride ink. The conductive ink may be printable.

The substrate layer may be a sheet or strip. The substrate layer is typically composed of an insulating polymer. The substrate layer may be composed of polyester, polycarbonate or polyvinyl chloride.

The carbon deposit on each conductive track may be deposited by known techniques such as printing (eg screen printing, silk screen printing, ink-jet printing or thick film printing), sputtering, lithography, vapour deposition, spray coating or vacuum deposition. The carbon deposit may be composed of inert carbon such as graphite, glassy carbon or pyrolytic carbon.

Typically the electrochemical sensor is interfaced with an instrument (preferably a portable field instrument) in a system which facilitates the electrochemical sensor to be operated amperometrically.

The electrochemical sensor may be integrated in an on-line system. Alternatively the electrochemical sensor may be portable. The electrochemical sensor may be single-use (eg disposable).

The aqueous solution may be potable water, recreational water, process water or waste water (eg industrial waste water). Preferred is potable water.

The sample of the aqueous solution may be brought into contact with the working electrode by dipping the working electrode into the sample of the aqueous solution or by dosing the sample of the aqueous solution onto the working electrode.

Typically the quantity of the oxidant of interest is its concentration.

Preferably the oxidant of interest is one or more of the group consisting of chlorine dioxide, chlorine, chlorite, hypochlorite, free chlorine, total chlorine, ozone, peracetic acid, hydrogen peroxide and monochloramine.

Particularly preferably the oxidant of interest is free chlorine and optionally total chlorine).

The reductant may be an iodide such as an alkali metal iodide (eg potassium iodide), N, N-diethyl-p-phenyldiamine (DPD) or tetramethylbenzidine (TMB).

The reagent formulation may further comprise one or more additives such as a buffer, gelling agent, thickening agent, wetting agent or stabiliser. Typical additives are one or more of the group consisting of sodium phosphate, potassium phthalate, sodium carbonate, disodium EDTA, hydroxyethylcellulose and polyvinylpyrrolidone. The reagent formulation may incorporate an acidic salt (eg sodium hydrogen sulphate) which in use reduces the pH to about 2.

The reagent formulation may take the form of a reagent layer. A reagent layer advantageously permits the redox reaction between the oxidant of interest and the reductant to occur intimately in situ.

The reagent formulation may be deposited and dried onto or near to the surface of either or both of the pair of working electrodes to form the reagent layer.

The reagent layer may include a porous matrix. The reagent layer may include a porous matrix impregnated with the reductant. The porous matrix may comprise polyvinylpyrrolidone and/or hydroxyethylcellulose. The reductant may be impregnated in the porous matrix by printing or microdosing.

In a preferred embodiment, the reagent formulation includes tetramethylbenzidine (TMB), a phosphate buffer and polyvinylpyrrolidone.

The present invention will now be described in a non-limitative sense with reference to the accompanying Figures in which.

Figure 1A:
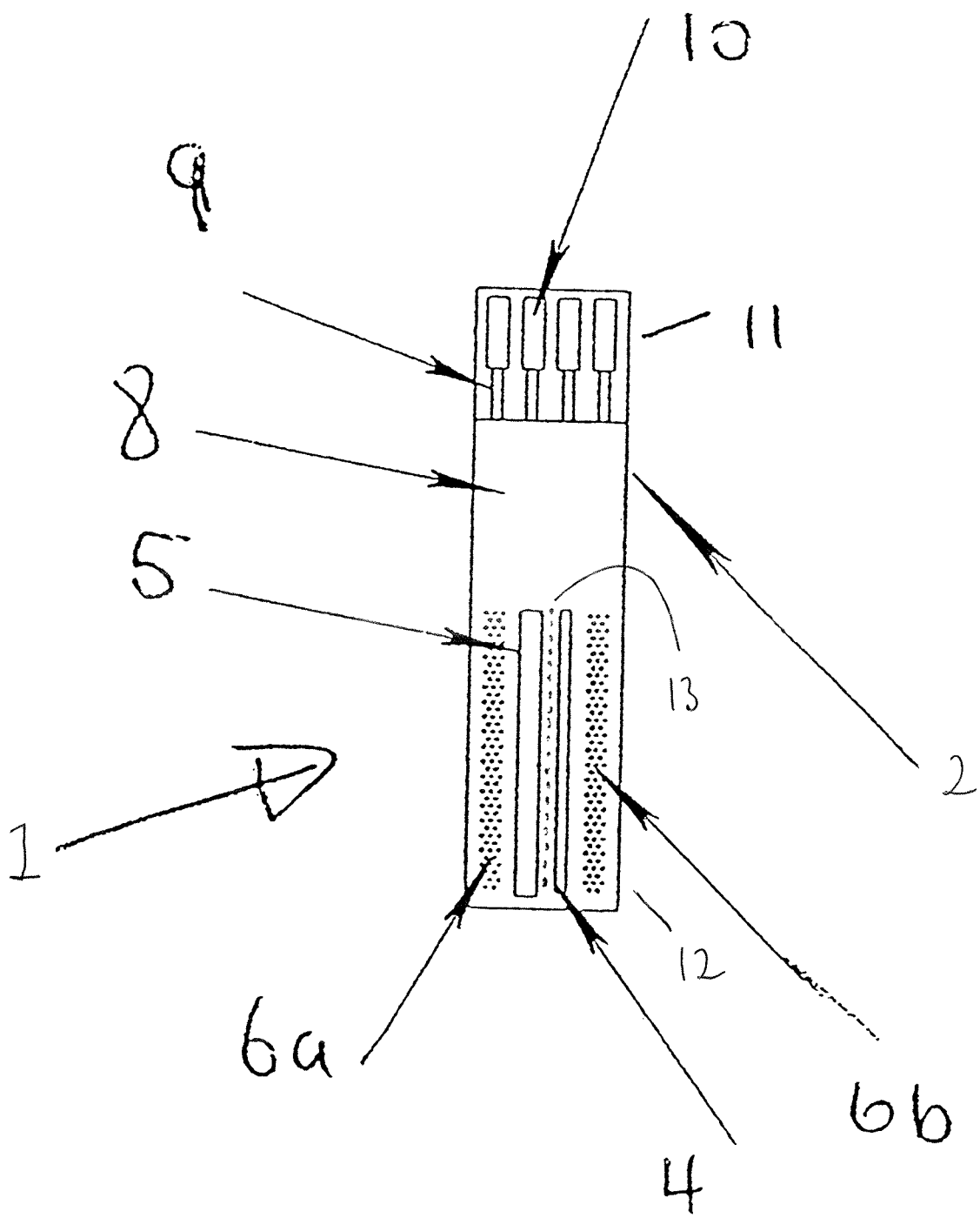
FIG. 1 illustrates a first embodiment of an electrochemical sensor of the invention in (a) plan view and (b) cross sectional view.
FIG. 1(c) illustrates schematically a second embodiment of an electrochemical sensor of the invention.
FIG. 1(d) illustrates schematically a third embodiment of an electrochemical sensor of the invention.
Figure 1:
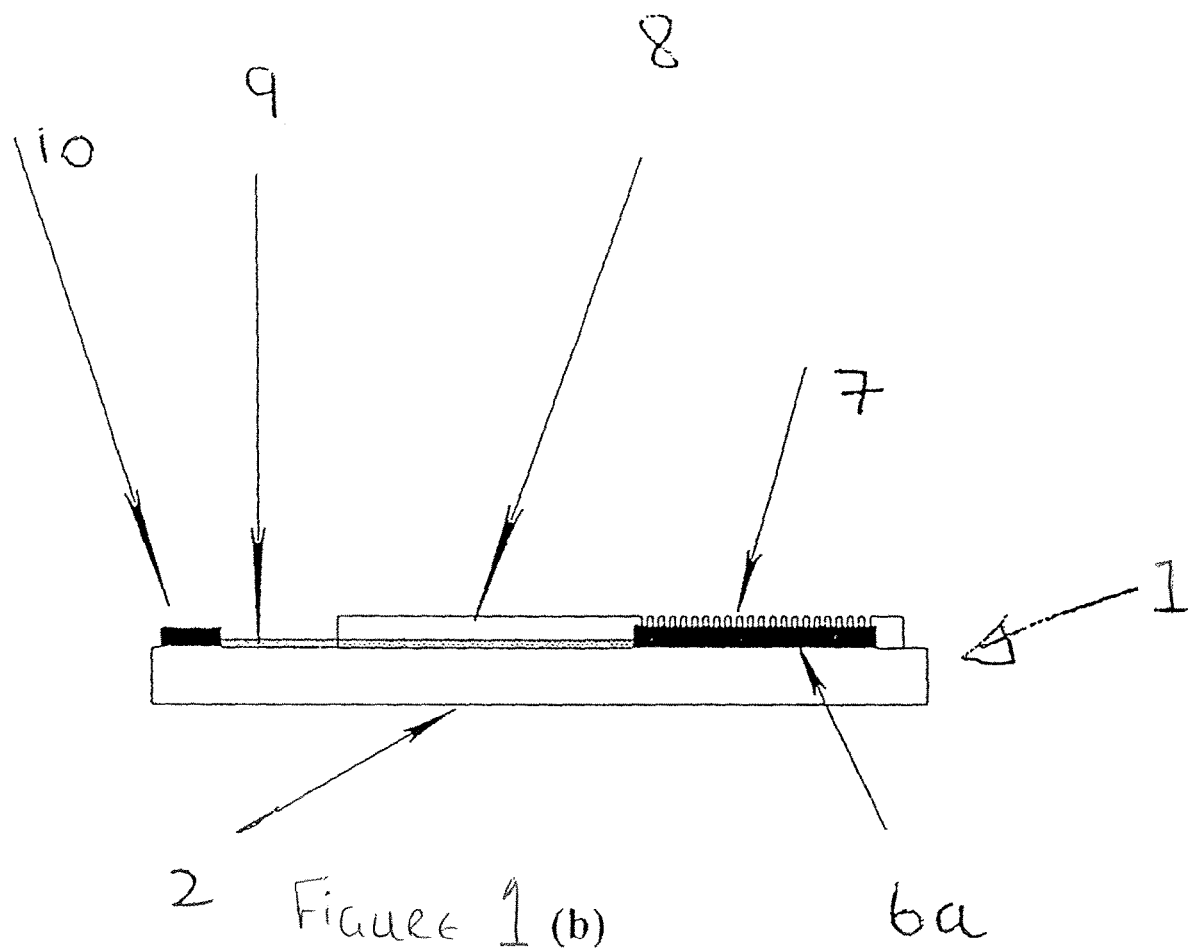

Shown in plan view in FIG. 1(a) and in cross section in FIG. 1(b) is a first embodiment of an electrochemical sensor of the invention 1 for the quantitative measurement of free chlorine and total chlorine in an aqueous sample. The electrochemical sensor 1 comprises a substrate in the form of a polymeric strip 2 on to which successive layers are deposited progressively by screen printing. A first successive layer is composed of four parallel spaced apart conductive tracks 9 of a highly conductive printable ink such as silver or silver/silver chloride. Each of the conductive tracks 9 terminates near to a first end 11 of the strip 2 in an electrical contact 10.

A first of the four conductive tracks 9 constitutes a reference electrode 4. On a second of the four conductive tracks 9 near to a second end 12 of the strip 2 is deposited carbon to form a counter electrode 5. On a third and fourth of the four conductive tracks 9 near to the second end 12 of the strip 2 is deposited carbon to form a pair of working electrodes 6a, 6b. The working electrodes 6a, 6b flank the reference electrode 4 and the counter electrode 5.

Over the top of each electrode 4, 5, 6a, 6b is screen printed first and second layers of non-conductive ink 8. During screen printing, a screen used to deposit the first layer of non-conductive ink 8 is such that the electrical contacts 10 and the electrodes 4, 5, 6a, 6b are left exposed. A screen is used to deposit the second layer of non-conductive ink 8 on the carbon deposit of each working electrode 6a, 6b in such a way as to describe an array of apertures 7. Each aperture exposes a discrete working region of the working electrode 6a, 6b which thereby constitutes 95 discrete disc electrodes. The reference electrode 4 and the counter electrode 5 near to the second end 12 of the strip are left exposed.

On the working electrode 6b is deposited a dried reagent formulation which provides the chemical components essential for the direct determination of free chlorine. The dried reagent formulation includes tetramethylbenzidine (TMB), a phosphate buffer and polyvinylpyrrolidone.

On the working electrode 6a is deposited a dried reagent formulation which provides the chemical components essential for the direct determination of total chlorine. The dried reagent formulation includes potassium iodide (0.5 g in 50 ml), potassium hydrogen phthalate (1.02 g in 50 ml) and carboxymethylcellulose (0.125 g in 50 ml).

Deposited onto the non-conductive ink 8 between the reference electrode 4 and the counter electrode 5 is a deposit 13 of sixteen doses of potassium chloride acting as a supporting electrolyte. The deposit 13 of doses is formed from a total volume of 3.2 µl of a 9.32 g/100 ml KCl solution dropped onto the non-conductive ink 8. The total mass of the deposit is 0.000298 g.

The electrochemical sensor 1 may be interfaced with a suitable portable field instrument (eg ChlordioXense, Palintest Ltd) to be operated amperometrically.

Figure 1C:
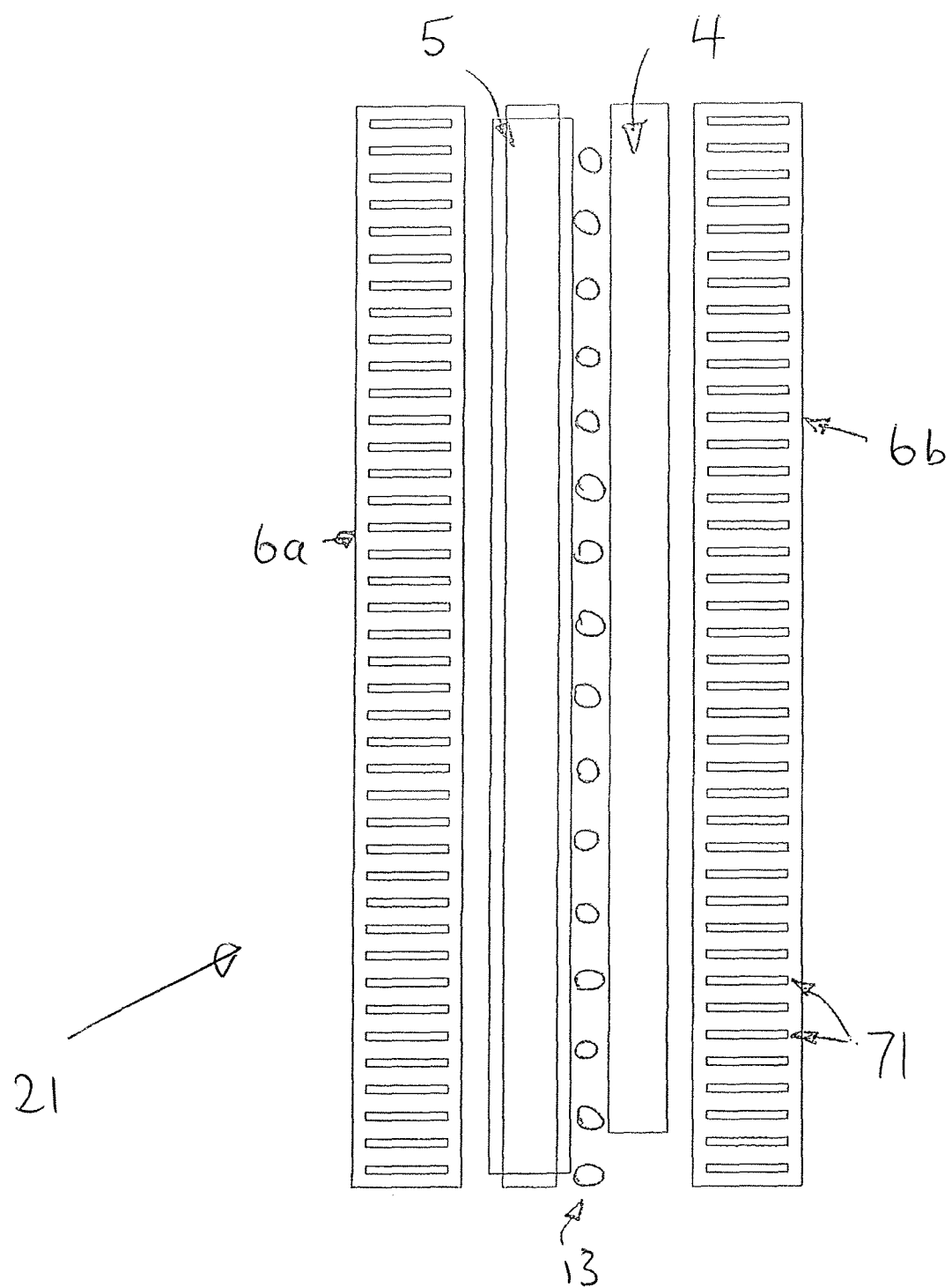

Shown schematically in FIG. 1(c) is a second embodiment of an electrochemical sensor of the invention 21 which is substantially identical to the first embodiment 1. However in the case of the second embodiment 21, the array of apertures constitutes multiple horizontal apertures (or microbands) 71.

Figure 1D:
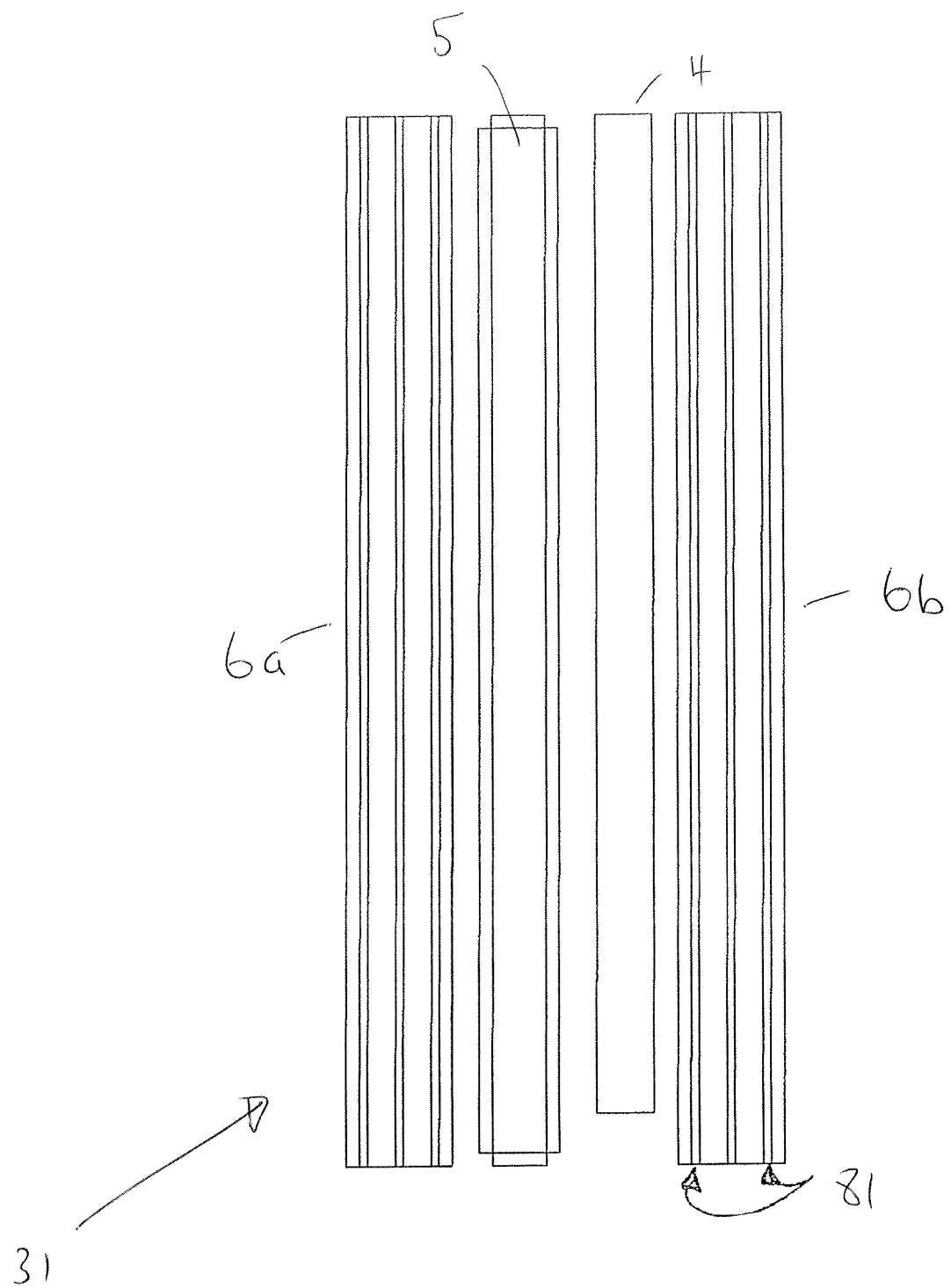

Shown schematically in FIG. 1(d) is a third embodiment of an electrochemical sensor of the invention 31 which is substantially identical to the first embodiment 1. However in the case of the third embodiment 31, the array of apertures constitutes multiple vertical apertures (or microbands) 81.

Current-Time Response Curves

When a 200 micron vertical microband electrochemical sensor of the type shown in FIG. 1(d) but without KCl deposit 13 is dosed with a dried reagent formulation and immersed in a test aqueous solution, the large difference in localised ionic strength between the boundary layer adjacent to the surface and the bulk solution gives rise to a convective plume emanating away from the surface. The effect of this plume on the current is demonstrated in FIG. 2B. It can be seen that the current-time response varies significantly for low chlorine test solutions (0.1 mg/L in FIG. 2B) and high chlorine test solutions (0.5 mg/L in FIG. 2B) and that there are inconsistent readings for multiple analyses of the same solution.

Figure 2:
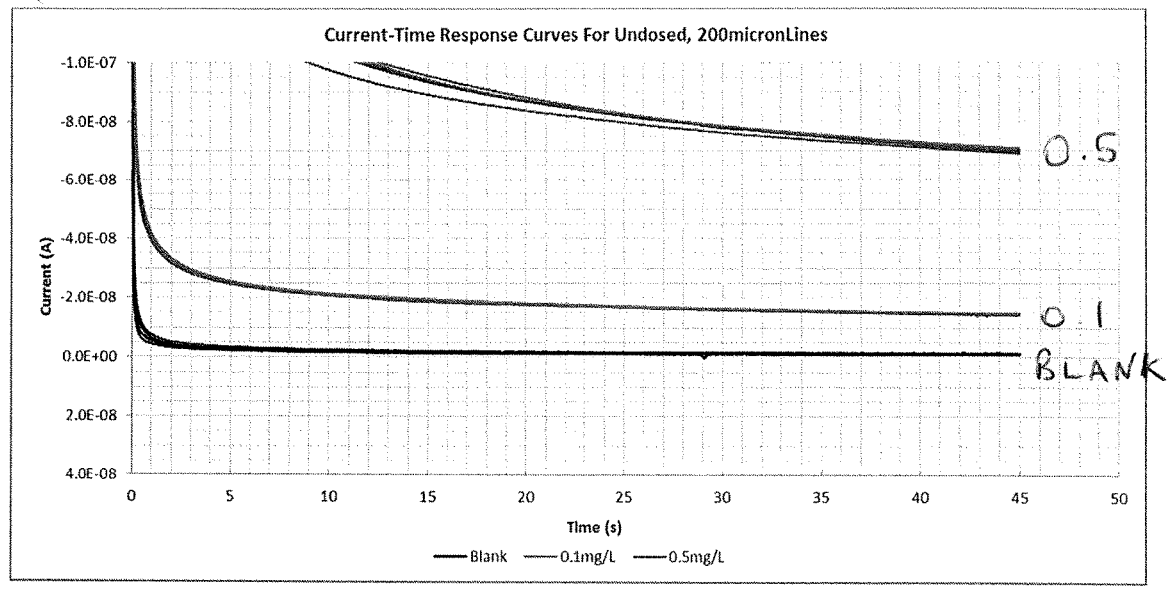
FIGS. 2A and 2B are current-time response curves for an electrochemical sensor with vertical microbands.
Figure 2:
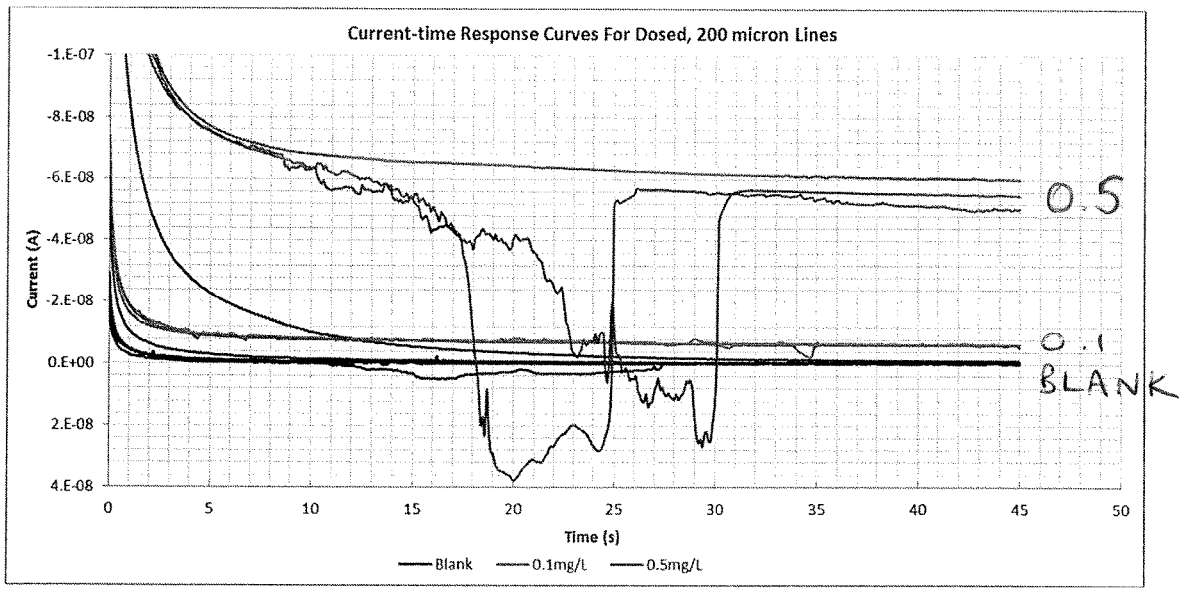

If the same experiment is carried out with no reagent formulation dosed onto the vertical microband electrochemical sensor and the equivalent concentration of reagents added to the bulk solution, no disruption of the steady state current is observed (see FIG. 2A). The conclusion is that the perturbation of the current response is a direct consequence of the presence of the reagent formulation at the surface of the working electrode.

Comparative Test 1

Figure 3:
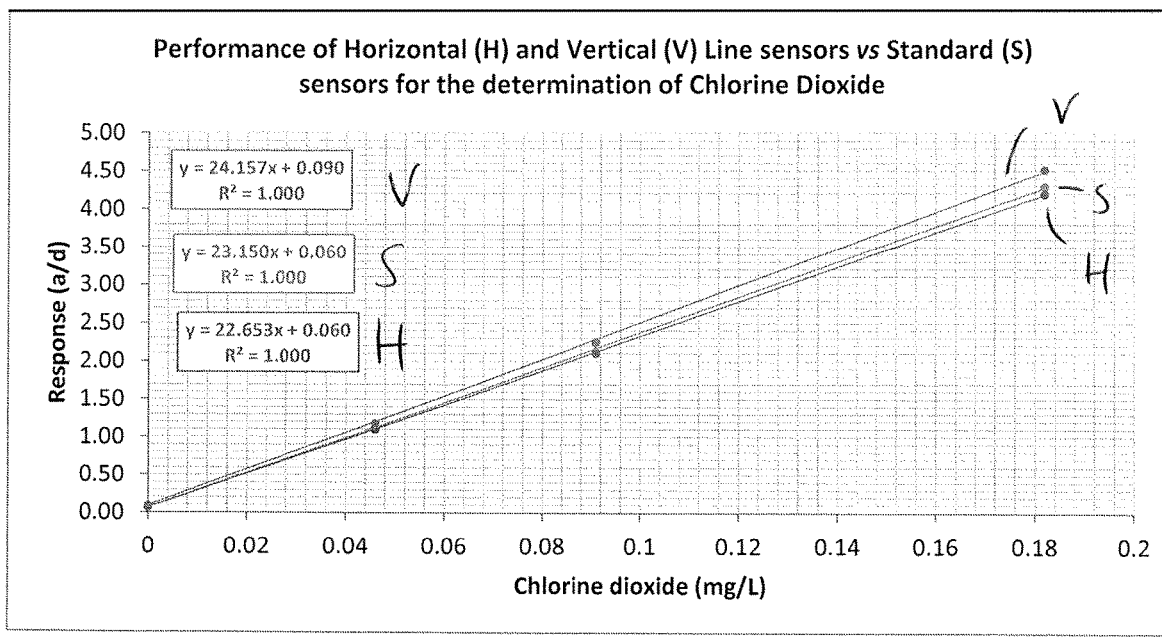
FIG. 3 illustrates the performance of sensors with standard circular (S), vertical (V) and horizontal (H) microbands for the determination of chlorine dioxide.

A standard 350 micron electrochemical sensor of the type disclosed in WO-A-2007/026152 with circular apertures and examples of a sensor with horizontal and vertical microbands were prepared without a reagent formulation and used for the determination of chlorine dioxide in solution. In all cases, the sensors were dosed with KCl as described above. They showed similar performance in terms of signal response per area and limit of detection (LOD). The results are shown in Table 1 and FIG. 3.

TABLE 1

Method Detection Limit (MDL) for sensors to determine Chlorine Dioxide

| Type | MDL (ppb) |
|---|---|
| Standard | 3.6 |
| Horizontal Line Sensor | 4.6 |
| Vertical Line Sensor | 4.9 |

Comparative Test 2

Figure 4:
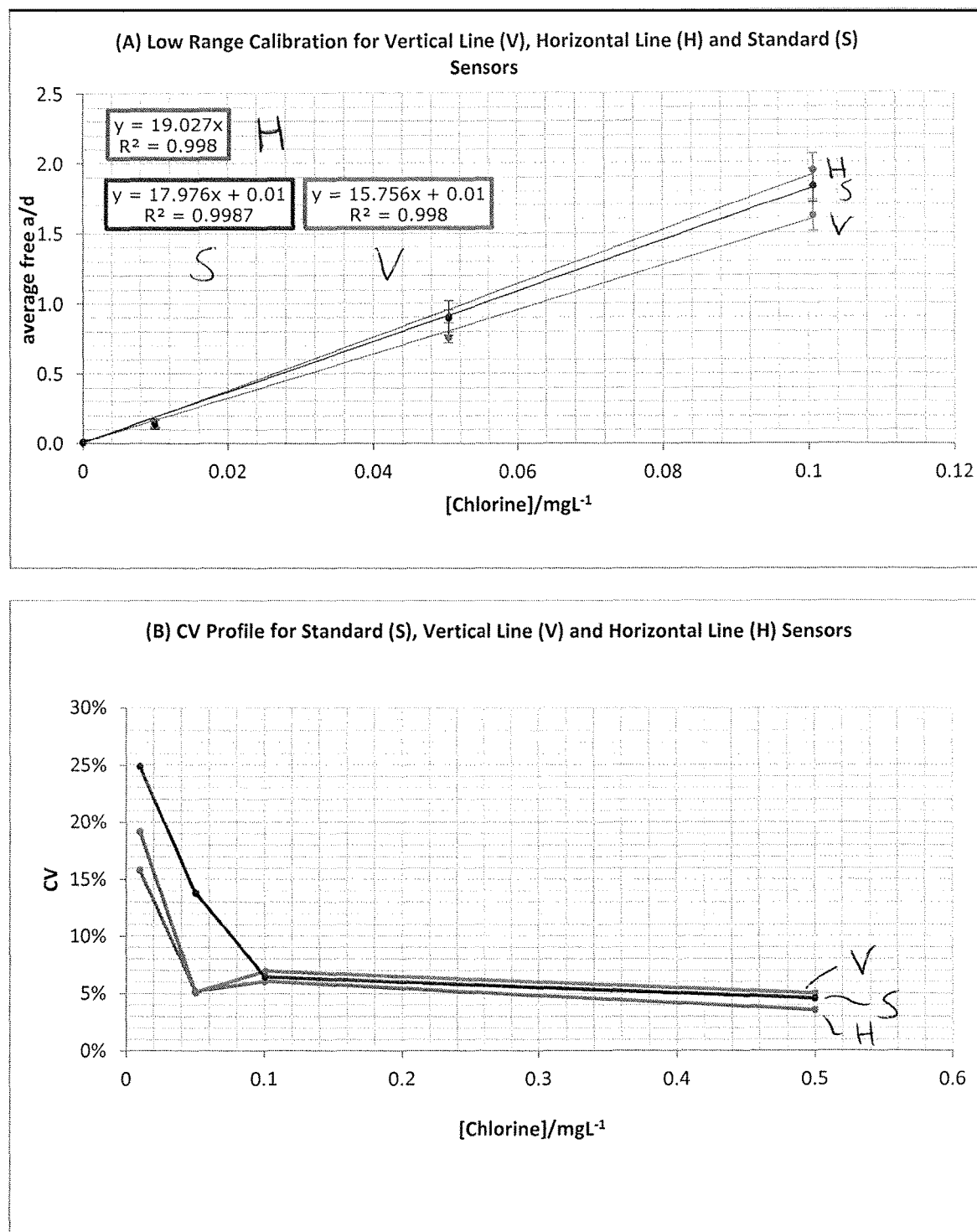
FIG. 4A illustrates the low range calibration for sensors with standard circular (S), vertical (V) and horizontal (H) microbands for the determination of chlorine.
FIG. 4B is the CV profile for sensors with standard circular (S), vertical (V) and horizontal (H) microbands for the determination of chlorine.

A standard 350 micron electrochemical sensor of the type disclosed in WO-A-2007/026152 and examples of a sensor with horizontal and vertical microbands were prepared with a reagent formulation and used for the determination of chlorine in solution. In all cases, the sensors were dosed with KCl as described above. The sensors with horizontal and vertical microbands showed improved LOD performance relative to the standard sensor with circular apertures (see Table 2 and FIGS. 4A and 4B).

TABLE 2

Free Chlorine

| [Chlorine]/mg/L | av_a/d free | sd | CV | LOD (ppb) |
|---|---|---|---|---|
| | Horizontal lines | | | |
| 0 | 0.00 | 0.005 | 387% | 16 (1) |
| 0.01 | 0.14 | 0.02 | 16% | 6 (2) |
| 0.0504 | 0.91 | 0.05 | 5.2% | |
| 0.1007 | 1.95 | 0.12 | 6.1% | |
| 0.5 | 12.36 | 0.44 | 3.5% | |
| | Vertical lines | | | |
| 0 | 0.01 | 0.017 | 149% | 19 (1) |
| 0.01 | 0.14 | 0.03 | 19% | |
| 0.0504 | 0.76 | 0.04 | 5.1% | 6 (2) |
| 0.1007 | 1.62 | 0.11 | 6.9% | |
| 0.5 | 9.82 | 0.49 | 5.0% | |
| | Standard | | | |
| 0 | 0.04 | 0.062 | 172% | 37 (1) |
| 0.01 | 0.11 | 0.1 | 44.8% | 20 (2) |
| 0.0504 | 0.89 | 0.1 | 15.7% | |

TABLE 2-continued

Free Chlorine

| [Chlorine]/mg/L | av_a/d free | sd | CV | LOD (ppb) |
|---|---|---|---|---|
| 0.1007 | 1.90 | 0.3 | 13.2% | |
| 0.5 | 11.84 | 0.4 | 3.7% | |

LOD—(1) determined from 0.1 mg/L data, (2) determined from 0.05 mg/L data

Figure 5:
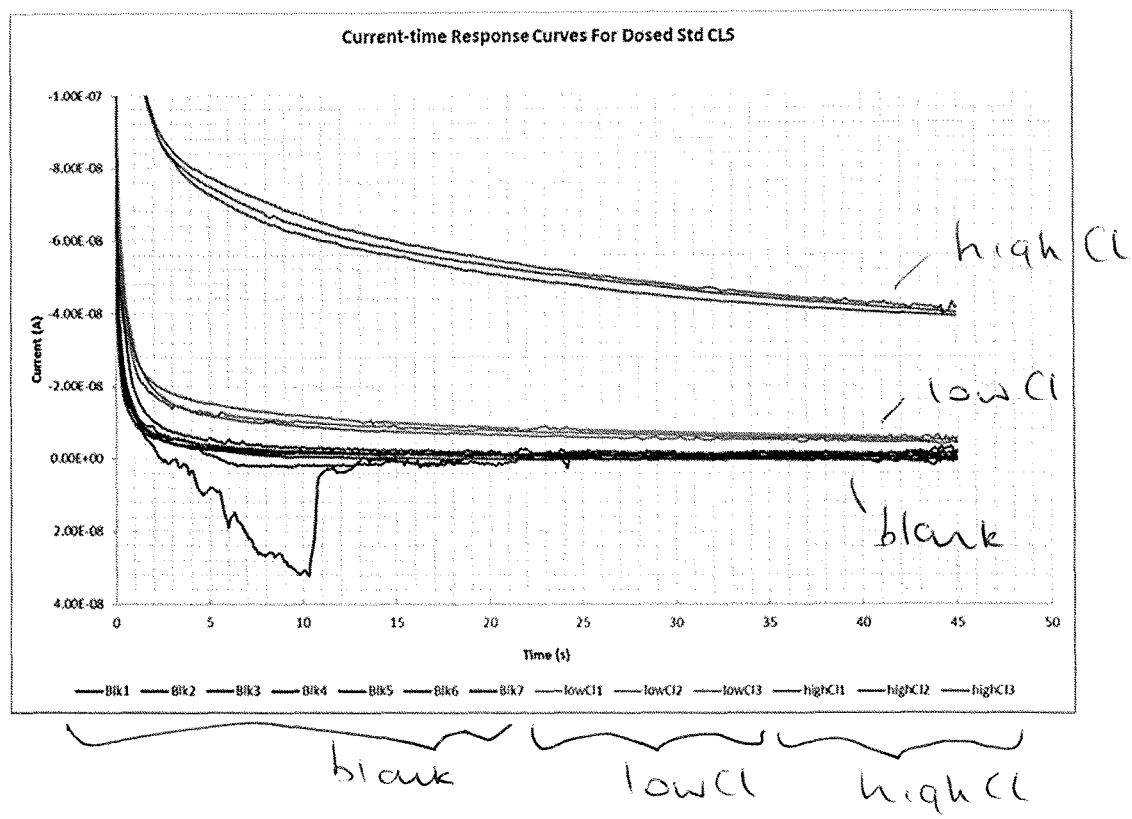
FIG. 5 are current-time response curves for (A) a standard electrochemical sensor and (B) an electrochemical sensor with vertical microbands.
Figure 5:
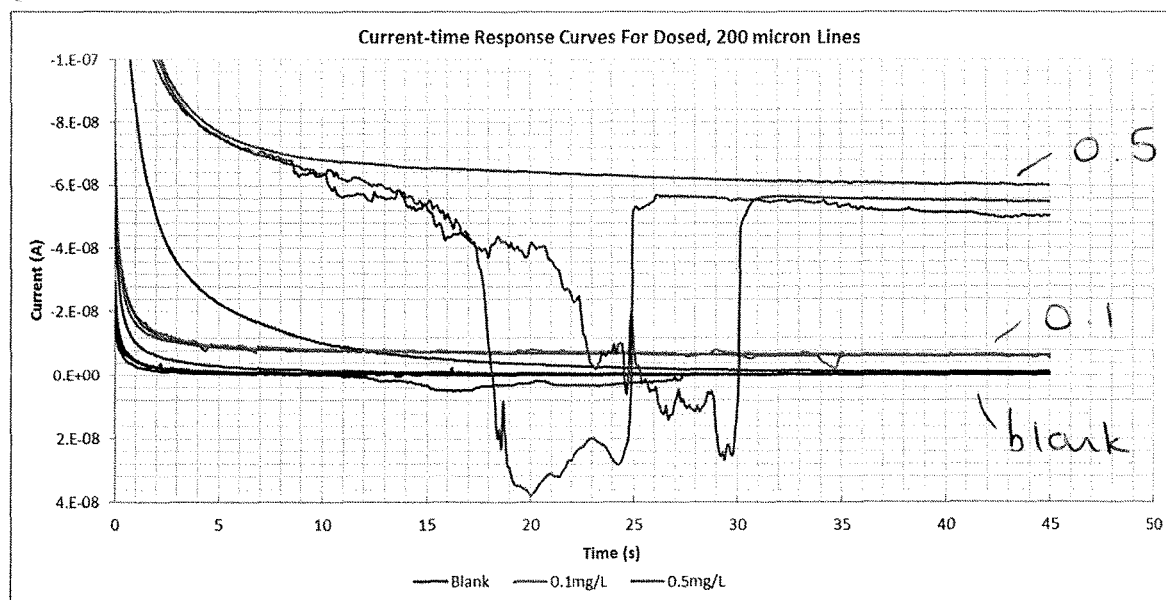
Figure 6:
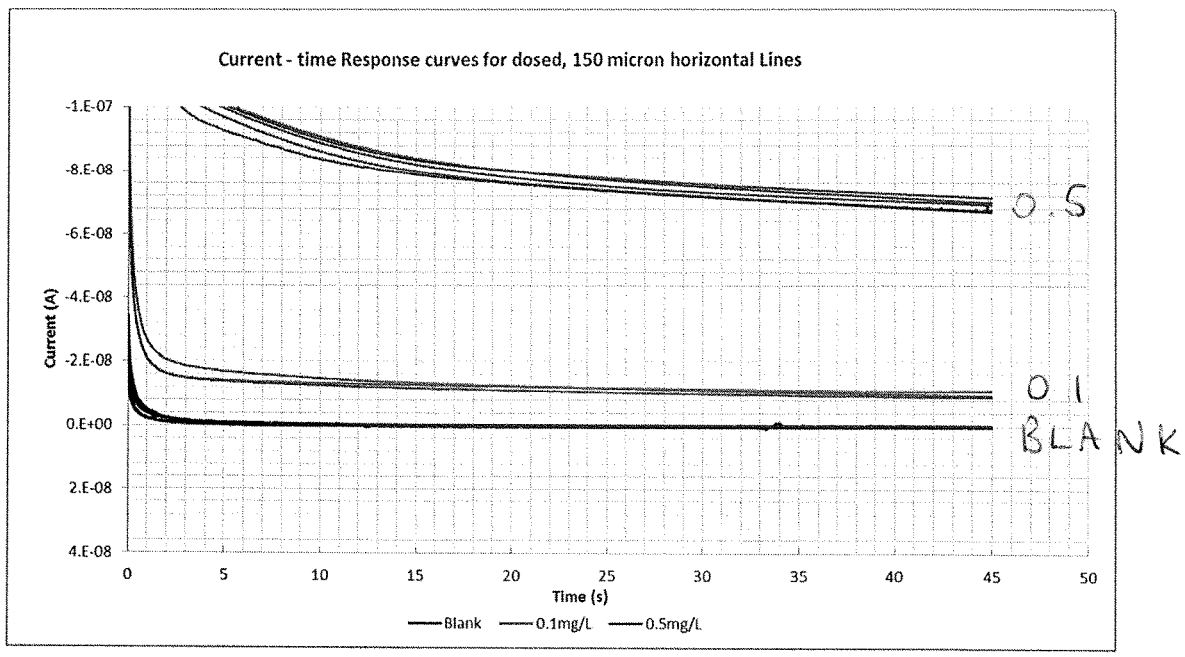
FIG. 6 is a current-time response curve for an electrochemical sensor with horizontal microbands.

During the determination of chlorine, a number of test results showed a deviation from the normal current-time response curve (see FIGS. 5A and 5B). These atypical responses for standard sensors and for sensors with vertical microbands are due to convection plumes arising from the presence of the reagent formulation at the electrode surface. It was evident that the size and severity of the plume was related to the vertical dimension of the electrode surface such that the circular electrodes of the standard sensor demonstrated less current variability than the vertical microband electrodes. This is explained by the dissolution of the reagent cascading down the surface disrupting the electrode boundary layer. Plumes were not observed on sensors with 150 micron horizontal microbands (see FIG. 6).

CONCLUSION

Studies on the electrochemical sensor 1 of the invention described above have shown that the deposit 13 of KCl acting as a supporting electrolyte deposited between the reference electrode 4 and the counter electrode 5 serves to inhibit the generation of plumes and ensure steady state readings. KCl does not take part in the electrochemical analysis. The dissolution of KCl into the bulk solution away from the first and second layer of non-conductive ink 8 reduces the difference in ionic strength between the boundary layer and bulk solution and limits the formation of convective plumes. This results in steady state currents and improves the capability of the electrochemical analysis.

The invention claimed is:

1. An electrochemical sensor for determining the presence or quantity of an oxidant of interest in an aqueous solution comprising:

an elongate substrate layer having a first end opposite to a second end;

first, second and third conductive tracks deposited axially onto the substrate layer in a parallel mutually spaced apart relationship, wherein the first conductive track constitutes a reference electrode, wherein on the second conductive track near to the second end of the substrate layer is a carbon deposit whereby to constitute a counter electrode and on the third conductive track near to the second end of the substrate layer is a carbon deposit whereby to constitute a working electrode, wherein each of the first, second and third conductive tracks terminates near to the first end of the substrate layer in an electrical contact;

a non-conductive layer deposited on the first, second and third conductive tracks, wherein the non-conductive layer is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposit of the third conductive track through an array of apertures;

a reagent formulation deposited on or near to the surface of the working electrode, wherein the reagent formulation includes a reductant; and a deposit of a supporting electrolyte deposited on the non-conductive layer, wherein the deposit of a supporting electrolyte is deposited on a region of the non-conductive layer between the fully exposed carbon deposit on the second conductive track and the fully exposed first conductive track.

2. The electrochemical sensor as claimed in claim 1, wherein the amount of the deposit of supporting electrolyte deposited on the non-conductive layer is sufficient in use to substantially remain within a boundary layer region at the surface of the nonconducting layer.

3. The electrochemical sensor as claimed in claim 1, wherein the amount of the deposit of supporting electrolyte deposited on the non-conductive layer is in excess of $2.0 \times 10^{-6}$ moles.

4. The electrochemical sensor as claimed in claim 1, wherein the amount of the deposit of supporting electrolyte deposited on the non-conductive layer is in the range $2.1 \times 10^{-6}$ to $6.0 \times 10^{-6}$ moles.

5. The electrochemical sensor as claimed in claim 1, wherein the deposit of supporting electrolyte deposited on the non-conductive layer is depositable from an aqueous solution of the supporting electrolyte with a molarity in excess of 0.626 mol/l.

6. The electrochemical sensor as claimed in claim 1, wherein the deposit of supporting electrolyte deposited on the non-conductive layer is depositable from an aqueous solution of the supporting electrolyte with a molarity in the range 0.63 to 1.90 mol/l.

7. The electrochemical sensor as claimed in claim 1, wherein the deposit of a supporting electrolyte is a plurality of doses of the supporting electrolyte deposited discretely on the non-conductive layer.

8. The electrochemical sensor as claimed in claim 1, wherein each aperture is elongate and substantially perpendicular to the first, second and third conductive track.

9. The electrochemical sensor as claimed in claim 1, further comprising: a fourth conductive track deposited axially onto the substrate layer,
wherein the first, second, third and fourth conductive track are in a parallel mutually spaced apart relationship, wherein on the fourth conductive track near to the second end of the substrate layer is a carbon deposit whereby the third and fourth conductive tracks constitute a pair of working electrodes, wherein the first and second conductive tracks are flanked by the third and fourth conductive tracks, wherein each of the first, second, third and fourth conductive tracks terminates near to the first end of the substrate layer in an electrical contact, wherein the non-conductive layer is deposited on the first, second, third and fourth conductive tracks and is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposits of the third and fourth conductive tracks through an array of apertures, wherein the reagent formulation is deposited on or near to the surface of either or both of the pair of working electrodes.

10. The electrochemical sensor as claimed in claim 9, wherein the plurality of doses is deposited in a parallel mutually spaced apart relationship to the first, second, third and fourth conductive track.

11. The electrochemical sensor as claimed in claim 9, wherein each aperture is elongate and substantially perpendicular to the first, second, third and fourth conductive track.

12. The electrochemical sensor as claimed in claim 1, wherein each aperture of the array of apertures is substantially rectangular.

13. The electrochemical sensor as claimed in claim 1, wherein the oxidant of interest is one or more of the group consisting of chlorine dioxide, chlorine, chlorite, hypochlorite, free chlorine, total chlorine, ozone, peracetic acid, hydrogen peroxide and monochloramine.

14. An electrochemical sensor for determining the presence or quantity of an oxidant of interest in an aqueous solution comprising:
an elongate substrate layer having a first end opposite to a second end;
first, second and third conductive tracks deposited axially onto the substrate layer in a parallel mutually spaced apart relationship, wherein the first conductive track constitutes a reference electrode, wherein on the second conductive track near to the second end of the substrate layer is a carbon deposit whereby to constitute a counter electrode and on the third conductive track near to the second end of the substrate layer is a carbon deposit whereby to constitute a working electrode, wherein each of the first, second and third conductive tracks terminates near to the first end of the substrate layer in an electrical contact;
a non-conductive layer deposited on the first, second and third conductive tracks, wherein the non-conductive layer is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposit of the third conductive track through an array of apertures;
a reagent formulation deposited on or near to the surface of the working electrode, wherein the reagent formulation includes a reductant; and
a deposit of a supporting electrolyte deposited on the non-conductive layer, wherein the supporting electrolyte is potassium chloride.

15. The electrochemical sensor as claimed in claim 14, wherein the amount of the deposit of supporting electrolyte deposited on the non-conductive layer is sufficient in use to substantially remain within a boundary layer region at the surface of the nonconducting layer.

16. The electrochemical sensor as claimed in claim 14, wherein the amount of the deposit of supporting electrolyte deposited on the non-conductive layer is in excess of $2.0 \times 10^{-6}$ moles.

17. The electrochemical sensor as claimed in claim 14, wherein the amount of the deposit of supporting electrolyte deposited on the non-conductive layer is in the range $2.1 \times 10^{-6}$ to $6.0 \times 10^{-6}$ moles.

18. The electrochemical sensor as claimed in claim 14, wherein the deposit of supporting electrolyte deposited on the non-conductive layer is depositable from an aqueous solution of the supporting electrolyte with a molarity in excess of 0.626 mol/l.

19. The electrochemical sensor as claimed in claim 14, wherein the deposit of supporting electrolyte deposited on the non-conductive layer is depositable from an aqueous solution of the supporting electrolyte with a molarity in the range 0.63 to 1.90 mol/l.

20. The electrochemical sensor as claimed in claim 14, wherein the deposit of a supporting electrolyte is a plurality of doses of the supporting electrolyte deposited discretely on the non-conductive layer.

21. The electrochemical sensor as claimed in claim 14, wherein each aperture is elongate and substantially perpendicular to the first, second and third conductive track.

22. The electrochemical sensor as claimed in claim 14, further comprising: a fourth conductive track deposited axially onto the substrate layer,
wherein the first, second, third and fourth conductive track are in a parallel mutually spaced apart relationship, wherein on the fourth conductive track near to the second end of the substrate layer is a carbon deposit whereby the third and fourth conductive tracks constitute a pair of working electrodes, wherein the first and second conductive tracks are flanked by the third and fourth conductive tracks, wherein each of the first, second, third and fourth conductive tracks terminates near to the first end of the substrate layer in an electrical contact, wherein the non-conductive layer is deposited on the first, second, third and fourth conductive tracks and is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposits of the third and fourth conductive tracks through an array of apertures, wherein the reagent formulation is deposited on or near to the surface of either or both of the pair of working electrodes.

23. The electrochemical sensor as claimed in claim 22, wherein the plurality of doses is deposited in a parallel mutually spaced apart relationship to the first, second, third and fourth conductive track.

24. The electrochemical sensor as claimed in claim 22, wherein each aperture is elongate and substantially perpendicular to the first, second, third and fourth conductive track.

25. The electrochemical sensor as claimed in claim 14, wherein each aperture of the array of apertures is substantially rectangular.

26. The electrochemical sensor as claimed in claim 14, wherein the oxidant of interest is one or more of the group consisting of chlorine dioxide, chlorine, chlorite, hypochlorite, free chlorine, total chlorine, ozone, peracetic acid, hydrogen peroxide and monochloramine.

* * * * *